(12) United States Patent
Marquillas Olondriz et al.

(10) Patent No.: US 8,604,242 B2
(45) Date of Patent: Dec. 10, 2013

(54) PROCESS FOR THE PREPARATION OF OPTICALLY ACTIVE (S)-(−)-2-(N-PROPYLAMINO)-5-METHOXYTETRALINE AND (S)-(−)-2-(N-PROPYLAMINO)-5-HYDROXYTETRALINE COMPOUNDS

(75) Inventors: Francisco Marquillas Olondriz, Sant Cugat Del Vallès (ES); Marta Pomares Marco, Sant Cugat Del Vallès (ES)

(73) Assignee: Interquim, S.A., Sant Cugat del Valles (ES)

( * ) Notice: Subject to any disclaimer, the term of this patent is extended or adjusted under 35 U.S.C. 154(b) by 131 days.

(21) Appl. No.: 13/059,650

(22) PCT Filed: Oct. 9, 2009

(86) PCT No.: PCT/EP2009/063207
§ 371 (c)(1),
(2), (4) Date: Feb. 18, 2011

(87) PCT Pub. No.: WO2010/043571
PCT Pub. Date: Apr. 22, 2010

(65) Prior Publication Data
US 2011/0152543 A1 Jun. 23, 2011

(30) Foreign Application Priority Data
Oct. 13, 2008 (ES) .................................. 200802890

(51) Int. Cl.
*C07B 57/00* (2006.01)
*C07C 211/00* (2006.01)
(52) U.S. Cl.
USPC .......................... 564/304; 564/305; 564/336
(58) Field of Classification Search
None
See application file for complete search history.

(56) References Cited

U.S. PATENT DOCUMENTS

| 4,564,628 | A | 1/1986 | Horn |
| 4,657,925 | A | 4/1987 | Horn |
| 4,885,308 | A | 12/1989 | Horn |
| 4,968,837 | A | 11/1990 | Manimaran et al. |
| 5,118,690 | A * | 6/1992 | Minchin et al. ............... 514/314 |
| 2007/0197480 | A1 | 8/2007 | Scheller et al. |
| 2008/0146622 | A1 | 6/2008 | Scheller |

FOREIGN PATENT DOCUMENTS

| WO | WO 90/13294 A1 | 11/1990 |
| WO | WO 2010/043571 A1 | 4/2010 |

OTHER PUBLICATIONS

Carlos Correa; Guidelines for the examination of pharmaceutical patents ("Pautas para el examen de patentes farmaceuticas") (patents law document).
Carlos Correa; Pautas para el examen de patentes farmaceuticas; (patent law document).
Exp. No. 000650-2001/DIN (Opposition in Peru), Sep. 19, 2011.
Wolfgang Thormann et al.; Capillary electrophoresis with (R)-(−)-N-(3,5-dinitrobenzoyl) . . . ; Journal of Pharmaceutical and Biomedical Analysis; 2002; vol. 27; pp. 555-567.
Chiral Resolving Agents; 2010: pp. 1-15; retrieved from the Internet: URL:http://www.sigmaaldrich.com/chemistry/chemistry•products.html. XP-002572390.
John D McDermed et al.; Synthesis and Dopaminergic Activity of . . . ; Journal of Medicinal Chemistry; vol. 19, No. 4: pp. 547-549; 1976.
Max P Seiler et al.; Structure-Activity Relationships of Dopaminergic . . . ; J. Med. Chem.; No. 29: pp. 912-917, 1986.
N. J. Cusack et al., N-0923. Dopamine D2 Agonist; Drugs of the Future: vol. 18: No. 11: pp. 1005-1008: Jan. 1, 1993 (XP008099004).
Ull Hacksell et al.; N-Alkylated 2-Aminotetralins Central Dopamine-Receptor Journal of Medicinal Chemistry; vol. 22; No. 12, pp. 1469-1475; 1979.

\* cited by examiner

*Primary Examiner* — Clinton Brooks
(74) *Attorney, Agent, or Firm* — Birch, Stewart, Kolasch & Birch, LLP

(57) ABSTRACT

The present invention describes a novel process for the preparation of optically active (S)-(−)-2-(N-propylamino)-5-methoxytetraline and (S)-(−)-2-(N-propylamino)-5-hydroxytetraline compounds based on the optical resolution of mixtures of the enantiomers of 2-(N-propylamino)-5-methoxytetraline and 2-(N-propylamino)-5-hydroxytetraline respectively. This process comprises (a) reacting a mixture of the enantiomers of said compounds with an optically active organic acid to form diastereoisomeric salts and separating the salts by crystallization. Said compounds are useful in the preparation of (6S)-(−)-5,6,7,8-tetrahydro-6-[propyl-(2-thienyl)ethyl]amino-1-naphthol (Rotigotine). Rotigotine is a dopamine agonist and is indicated for the treatment of Parkinson's disease.

14 Claims, No Drawings

PROCESS FOR THE PREPARATION OF OPTICALLY ACTIVE (S)-(−)-2-(N-PROPYLAMINO)-5-METHOXYTETRALINE AND (S)-(−)-2-(N-PROPYLAMINO)-5-HYDROXYTETRALINE COMPOUNDS

FIELD OF THE INVENTION

The invention relates to a process for the preparation of optically active (S)-(−)-2-(N-propylamino)-5-methoxytetraline compounds, hereinafter referred to as S-(II), and (S)-(−)-2-(N-propylamino)-5-hydroxytetraline, hereinafter referred to as S-(III), with a high degree of optical purity, from a mixture of the enantiomers of 2-(N-propylamino)-5-methoxytetraline (II) and 2-(N-propylamino)-5-hydroxytetraline (III) respectively, using optical resolution via diastereomeric salt formation with an optically active acid.

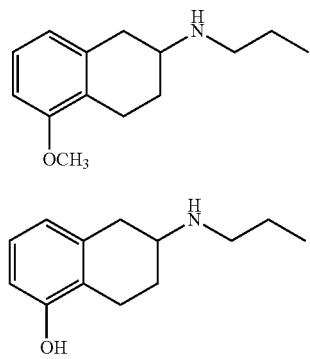

Intermediate compounds S-(II) and S-(III) are useful for the preparation of (6S)-(−)-5,6,7,8-tetrahydro-6-[propyl-(2-thienyl)ethyl]amino-1-naphthol (Rotigotine).

BACKGROUND OF THE INVENTION

U.S. Pat. No. 4,564,628 describes alkyl derivatives of aminotetraline exhibiting dopaminergic activity. Among these compounds, (I) is found,

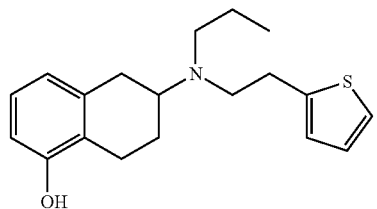

Subsequent studies, whose results are described in U.S. Pat. No. 4,657,925, show that the dopaminergic action of enantiomer (6S)-(−)-5,6,7,8-tetrahydro-6-[propyl-(2-thienyl)ethyl]amino-1-naphthol, hereinafter referred to as S-(I), is up to 140 times higher than that of enantiomer (6R)-(+)-5,6,7,8-tetrahydro-6-[propyl-(2-thienyl)ethyl]amino-1-naphthol.

U.S. Pat. No. 4,885,308 describes the use of S-(I), active ingredient known as Rotigotine, for the treatment of Pakinson's disease.

There is, therefore, a need for a process to prepare an optically pure S-(I) enantiomer, which is free of the R-(I) enantiomer.

The processes described so far for the preparation of S-(I) are based on the preparation of intermediate compound (S)-2-(N-propylamino)-5-methoxytetraline, S-(II).

U.S. Pat. No. 4,657,925 discloses the preparation of (S)-2-(N-propylamino)-5-methoxytetraline, S-(II), by resolution of the corresponding racemic mixture. However, no details on the resolution process used are given.

Hoeve et al., J. Org. Chem., 1985, vol. 50, p. 4508-4515, describe the preparation of S-(II) by optical resolution of the racemic mixture by using chiral (R)-(+)-4-(2-chlorophenyl)-5,5-dimethyl-2-hydroxy-1,3,2-dioxaphosphorinano-2-oxide phosphoric acid as an agent for racemic resolution. This methodology is expensive and tedious since it requires the preparation of said agent, which in turn involves an optical resolution step.

Seiler et al., J. Med. Chem., 1986, vol. 29, p. 912-917, describe the preparation of S-(II) by propylation and subsequent debenzylation of (S)-(−)-2-(N-benzylamino)-5-methoxytetraline, a compound whose preparation is described by McDermed et al. J. Med. Chem., 1976, vol. 19, 4, 547-549, by reductive amination of 5-methoxytetralone with benzylamine, crystallization of the diastereoisomeric salt of (−)-mandelic acid enriched in the (S)-enantiomer, optical purification of this salt by means of six successive recrystallizations in ether and finally the release of the amine as a base. The process is time-consuming and costly for its industrial application.

U.S. Pat. No. 4,968,837 describes the resolution of intermediate compound (II) in its enantiomers by using L-(−)-dibenzoyltartaric acid, although—according to the authors' experience of the present invention—a high optical purity cannot be achieved by applying this method, even after successive purifications of the diastereoisomeric salt.

As set out above, none of the preparation methods for S-(II) and, consequently, for S-(I) described so far seems to be satisfactory for its industrial application. There is, therefore, a need to provide an alternative industrial application process for the preparation of rotigotine, S-(I).

SUMMARY OF THE INVENTION

The invention confronts with the problem of providing an alternative process susceptible of being applied at industrial level for the preparation of compound (6S)-(−)-5,6,7,8-tetrahydro-6-[propyl-(2-thienyl)ethyl]amino-1-naphthol, S-(I), with a high optical purity that affords its use as a medicament.

The solution provided in this invention is based on the fact that the inventors have observed that some optically active organic acids are capable of forming diastereoisomeric salts of different solubility in the reaction medium along with (II), R-(II) and S-(II) enantiomers and (III), R-(III) and S-(III) enantiomers, which allows their separation by crystallization. On allowing crystallization of the mixture of these diastereoisomeric salts in the reaction medium or in a suitable solvent, due to their different solubility, the formed crystals will be enriched in the diastereoisomeric salts of S-(II) and S-(III) enantiomers, which are useful intermediate compounds for the preparation of S-(I). The separation and purification of the diastereoisomeric salts and their subsequent release yields these intermediates with a high degree of optical purity.

The process of this invention allows obtaining intermediate compounds S-(II) and S-(III) with an optical purity similar to or higher than 99%, preferably higher than 99.9%, by means of successive recrystallizations or resuspensions of the corresponding diastereoisomeric salts.

DETAILED DESCRIPTION OF THE INVENTION

Compounds (II) and (III), in their racemic form, can be prepared by any of the methods described in the literature, for example, through the processes described by Hacksell et al., *J. Med. Chem.*, 1979, vol. 22(12), p. 1469-1475, from the reductive amination of 5-methoxy-2-tetralone with 1-propylamine to afford (II), and subsequent deprotection of the phenol group with 48% HBr to afford (III).

The synthetic pathway for the preparation of intermediate compounds S-(II) and S-(III)—the object of the present invention—is shown in Scheme 1:

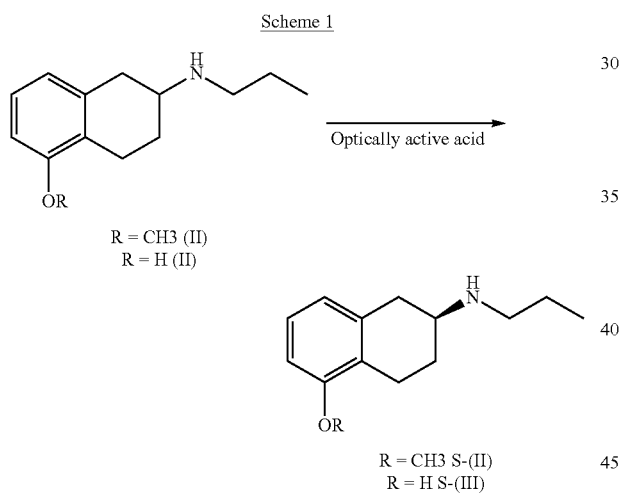

The process for the preparation of the S-(II) enantiomer provided in this invention is carried out via optical resolution by treating the mixture of (II) enantiomers with (+)-N-(3,5-dinitrobenzoyl)-α-phenylglycine acid in a suitable solvent. The obtained salt can be recrystallized or resuspended as many times as necessary to obtain the desired optical purity. Subsequently, the amine can be released from the formed salt and obtained S-(II) as a free base.

The process for the preparation of the S-(III) enantiomer provided in this invention is carried out via optical resolution by treating the mixture of (III) enantiomers with (−)-N-(3,5-dinitrobenzoyl)-α-phenylglycine acid in a suitable solvent. The obtained salt can be recrystallized or resuspended as many times as necessary to obtain the desired optical purity. Subsequently, the amine can be released from the formed salt and S-(III) can be obtained as a free base.

Precipitation of these diastereoisomeric salts and subsequent recrystallizations or resuspensions may take place in suitable solvents such as water, alcohols, nitriles or mixtures thereof. In a particular embodiment, this solvent is a mixture of acetonitrile and water.

The proportion of optically active organic acid to be added may be from about 0.5 to about 1.2 equivalents, preferably from about 0.6 to 1, in relation to the starting amine.

It is also an object of the invention to provide the salts of said intermediate compounds S-(II) and S-(III) with optically active (−)-N-(3,5-dinitrobenzoyl)-α-phenylglycine and (+)-N-(3,5-dinitrobenzoyl)-α-phenylglycine acids, according to the following structures (V) and (VI), respectively.

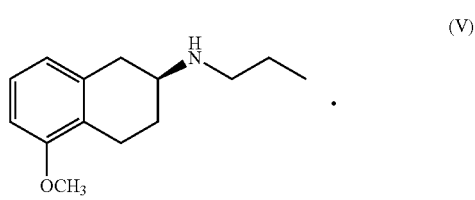

(V)

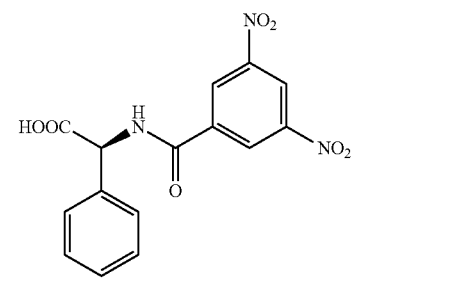

(VI)

It is, likewise, an object of the present invention the provide the use of compounds S-(II) and S-(III) thus obtained as intermediates in the preparation of rotigotine, S-(I), according to Scheme 2:

Scheme 2

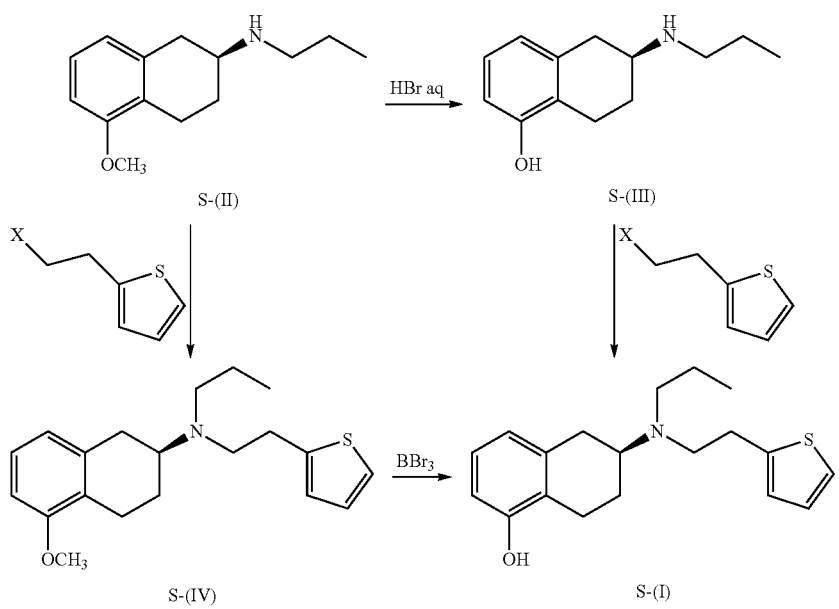

wherein X is a suitable leaving group selected from halogens, such as chlorine or bromine, sulfonates, such as mesylate, nosylate or tosylate, and the like.

Similarly, it is the object of the present invention to provide the use of (V) and (VI) salts as intermediate compounds in the preparation of rotigotine, S-(I).

Embodiments Of The Invention

The following examples are additionally given to illustrate the present invention and are not intended to limit the scope of the invention.

EXAMPLE 1

Preparation of (S)-(−)-2-(N-propylamino)-5-methoxytetraline, S-(II), from the racemic mixture, by optical resolution with (+)-N-(3,5-dinitrobenzoyl)-α-phenylglycine 10 g of (II) were dissolved in 120 mL of an acetonitrile-water mixture (60:40). Then, 9.4 g (0.6 equivalents) of (+)-N-(3,5-dinitrobenzoyl)-α-phenylglycine were added. The mixture was heated until dissolution. After the mixture was slowly cooled, turbidity appeared first and then a solid precipitate appeared. The mixture was left to stand at 0-5° C. for 2 hours. The suspension was filtered off and the resulting solid was oven dried.

9.8 g of the salt (38% yield) were obtained. The resultant product was analyzed by HPLC and showed an S-(II)/R-(II) enantiomer ratio of 83:17.

The solid was recrystallized successively in 10 volumes of an acetonitrile-water mixture (80:20), heated to reflux and then cooled to 0-5° C. After three recrystallizations, 3.8 g (15% overall yield) of salt (V) were obtained which by chiral HPLC showed an (S)-enantiomer ratio higher than 99.5%.

Melting point (DSC peak): 220.27° C.

IR (cm$^{-1}$, KBr): 3423, 2955, 2838, 1664, 1621, 1585, 1542, 1345, 731, 705

$^1$H-NMR (dmso-d$_6$) δ: 0.88 (t, 3H), 1.54-1.63 (m, 3H), 2.14 (m, 1H), 2.42 (m, 1H), 2.75 (m, 2H), 2.83 (t, 2H), 3.03 (dd, 1H), 3.18 (m, 1H), 3.35 (s wide, 2H, NH$_2$$^+$), 3.73 (s, 3H, OCH$_3$), 5.25 (d, 1H, CH—COOH), 6.62 (d, 1H, Ar—H), 6.74 (d, 1H, Ar—H), 7.07 (t, 1H, Ar—H), 7.16 (m, 1H, Ar—H), 7.23 (t, 2H, Ar—H), 7.45 (d, 2H, Ar—H), 8.91 (s, 1H, Ar—H) 9.03 (s, 2H, Ar—H), 9.42 (d, 1H, NH amide)

The purified dry salt was suspended under stirring in a mixture of toluene (20 mL) and 5% K$_2$CO$_3$ (60 mL) and heated to 60° C. until complete dissolution. The layers were separated and the organic layer was washed with 5% K$_2$CO$_3$ (15 mL), followed by water (8 mL). The organic layer was concentrated until the solvent was completely removed. 1.44 g of S-(II) was obtained as an oil (98% yield).

IR (cm$^{-1}$, NaCl): 2955, 2930, 2834, 1586, 1469, 1438, 1260, 1095, 766

$^1$H-NMR (CDCl$_3$) δ: 0.92 (t, 3H, CH$_2$—CH$_3$), 1.48-1.60 (m, 3H, CH$_2$—CH$_2$—CH$_3$ and N—CH—CH$_2$—CH$_2$—C), 1.80 (s wide, 1H, NH), 2.07 (m, 1H, N—CH—CH$_2$—CH$_2$—C), 2.50-2.61 (m, 2H, C—CH$_2$—CHN y N—CH—CH$_2$—C), 2.66 (t, 2H, CH$_2$—CH$_2$—CH$_3$), 2.84-2.93 (m, 2H, C—CH$_2$—CHN y N—CH—CH$_2$—CH$_2$—C), 2.95-3.10 (dd, 1H, C—CH$_2$—CHN) 3.78 (s, 3H, OCH$_3$), 6.63 (d, 1H, Ar—H), 6.68 (d, 1H, Ar—H), 7.07 (t, 1H, Ar—H)

The rotatory power of the product obtained was [α]$^{20}$$_D$: −73.49 (c=1 in methanol). As described in U.S. Pat. No. 4,968,837 as −65 and in Seiler, M. P. et al., *J. Med. Chem.* 1986, 29 (6), 912-917, as −72.7 (c=1 in methanol).

EXAMPLE 2

Preparation of (S)-(−)-2-(N-propylamino)-5-hydroxytetraline, S-(III), from the racemic mixture, by optical resolution with (−)-N-(3,5-dinitrobenzoyl)-α-phenylglycine A suspension of 10 g of (III) and 11.7 g (0.7 equivalents) of (−)-N-(3,5-dinitrobenzoyl)-α-phenylglycine in 160 mL of an acetonitrile-water mixture (70:30) was heated until dissolution. The solution formed was slowly cooled, turbidity appeared first and then a solid precipitate appeared. The mixture was left to stand at 0-5° C. for 2 hours. The suspension was filtered off and the resulting solid was dried.

11.2 g of the salt (42% yield) were obtained. The resultant product was analyzed by HPLC and showed an S-(III)/R-(III) enantiomer ratio of 91:9.

The solid was recrystallized successively in 10 volumes of an acetonitrile-water mixture (80:20), heated to reflux and then cooled to 0-5° C. After two recrystallizations, 6.0 g (24% overall yield) of salt (VI) were obtained which by chiral HPLC showed an (S)-enantiomer ratio higher than 99.9%.

IR (cm$^{-1}$, KBr): 3450, 3032, 2972, 2854, 1652, 1621, 1539, 1467, 1376, 1275, 729

$^1$H-NMR (dmso-d$_6$) δ: 0.87 (t, 3H), 1.53-1.62 (m, 3H), 2.13 (m, 1H), 2.39 (m, 1H), 2.72 (m, 2H), 2.83 (t, 2H), 3.00 (dd, 1H), 3.18 (m, 1H), 3.35 (s wide, 2H, NH$_2$$^+$), 5.23 (d, 1H, CH—COOH), 6.46 (d, 1H, Ar—H), 6.58 (d, 1H, Ar—H), 6.87 (t, 1H, Ar—H), 7.17 (m, 1H, Ar—H), 7.24 (t, 2H, Ar—H), 7.44 (d, 2H, Ar—H), 8.91 (s, 1H, Ar—H) 9.03 (d, 2H, Ar—H), 9.41 (d, 1H, NH amide), 9.55 (s, 1H, OH)

The purified dry salt was suspended under stirring in a mixture of toluene (20 mL) and 5% K$_2$CO$_3$ (60 mL) and heated to 60° C. until complete dissolution. The layers were separated and the organic layer was washed with 5% K$_2$CO$_3$ (15 mL), followed by water (8 mL). The organic layer was concentrated until the solvent was completely removed. 1.8 g of S-(III) was obtained as a solid (98% yield).

Melting point (DSC peak): 88.3° C.

IR (cm$^{-1}$, KBr): 3532, 3269, 2923, 2854, 1585, 1464, 1281, 773

$^1$H-NMR (dmso-d$_6$) δ: 0.86 (t, 3H), 1.40 (m, 3H), 1.94 (m, 1H), 2.38 (m, 2H), 2.53 (t, 2H), 2.69 (m, 2H), 2.84 (dd, 1H), 3.36 (s wide, 1H, NH), 6.46 (d, 1H, Ar—H), 6.54 (d, 1H, Ar—H), 6.84 (t, 1H, Ar—H), 9.08 (s, 1H, OH)

Rotatory power [α]$^{20}_D$: −74.89 (c=1 in methanol). Described in Seiler, M. P. et al., *J. Med. Chem.* 1986, 29 (6), 912-917, as −75.

EXAMPLE 3

Preparation of (S)-(−)-2-(N-propylamino)-5-hydroxytetraline, S-(III), from (S)-(−)-2-(N-propylamino)-5-methoxytetraline, S-(II)

10 g of (S)-(−)-2-(N-propylamino)-5-methoxytetraline, S-(II), obtained according to Example 1 were mixed with 40 mL of 48% HBr and 20 mL of acetic acid. The resulting mixture was refluxed for 3 hours. During this time period, precipitation of a solid began. The suspension was gradually cooled to 0-5° C. and 30 mL of water were added. The reaction mixture was filtered off and 11.7 g (90% yield) of S-(−)-2-(N-propylamino)-5-hydroxytetraline bromohydrate were obtained.

This solid was suspended in 110 mL of water and the suspension was heated to 40° C. 10M NaOH was added until the pH was 12.5, and the mixture became a solution. Later, the mixture was acidified to pH 9-9.5 with 6M HCl, and precipitation of a solid occurred. The mixture was gradually cooled to 0-5° C. and filtered off. 7.5 g of S-(−)-2-(N-propylamino)-5-hydroxytetraline, S-(III) were obtained (90% yield).

Melting point (DSC peak): 88.25° C.

Rotatory power [α]$^{20}_D$: −74.95 (c=1 in methanol).

EXAMPLE 4

Preparation of (6S)-(−)-5,6,7,8-tetrahydro-6-[propyl-(2-thienyl)ethyl]amino-1-naphthol, S-(I), from S-(−)-2-(N-propylamino)-5-hydroxytetraline, S-(III)

10 g of (S)-(−)-2-(N-propylamino)-5-hydroxytetraline, S-(III), obtained according to Example 2 were mixed with 9 g of NaHCO$_3$ (2.2 equivalents) and 16 g of 2-(2-thienyl)ethanol 2-nitrobenzenesulfonate (1.05 equivalents) in 80 mL of acetonitrile. The mixture was refluxed for 9 hours, and then cooled and filtered for removal of suspended salts. 60 mL of water were added to the filtrate and concentrated by distillation for removal of acetonitrile. 40 mL of toluene were added and the layers were separated. The organic layer was twice washed with 10% NaHCO$_3$. Then, 50 mL of water and H$_3$PO$_4$ were added to pH=1-2. After layer separation, the aqueous acid layer was neutralized with 30% K$_2$CO$_3$ to pH=7-7.5 and extracted with 20 mL of ethyl acetate. The organic layer was washed with 10 mL of water, concentrated by distillation from the solvent to provide 10 g of (6S)-(−)-5,6,7,8-tetrahydro-6-[propyl-(2-thienyl)ethyl]amino-1-naphthol, S-(I), as a white solid (70% yield).

Melting point (DSC peak): 78.94° C.

IR (cm$^{-1}$, KBr): 3500, 3098, 3065, 2969, 2932, 1585, 1465, 1281, 775, 701

$^1$H NMR (CDCl$_3$) δ: 0.89 (t, 3H, N—CH$_2$—CH$_2$—CH$_3$); 1.51 (sextuplet, 2H, N—CH$_2$—CH$_2$—CH$_3$); 1.58 (ddd, 1H, N—CH—CH$_2$—CH$_2$—C); 2.10 (ddd, 1H, N—CH—CH$_2$—CH$_2$—C); 2.55 (t, 2H, N—CH$_2$—CH$_2$—CH$_3$); 2.47-2.60 (m, 1H, C—CH$_2$—CHN); 2.67-2.87 (m, 4H, N—CH—CH$_2$—CH$_2$—C y N—CH$_2$—CH$_2$-thiophene); 2.90 (m, 1H, C—CH$_2$—CHN); 2.92-3.01 (m, 3H, C—CH$_2$—CHN y N—CH$_2$—CH$_2$— thiophene); 4.83 (s, 1H, OH); 6.57 (d, 1H, Ar—H); 6.67 (d, 1H, Ar—H); 6.80 (d, 1H, Ar—H); 6.90 (dd, 1H, Ar—H); 6.97 (t, 1H, Ar—H); 7.10 (d, 1H, Ar—H)

EXAMPLE 5

Preparation of (S)-2-(N-n-propyl-N-2-thienylethylamino)-5-methoxytetraline bromohydrate, S-(IV) .HBr, from (S)-(−)-2-(N-propylamino)-5-methoxytetraline, S-(II)

10 g of (S)-(−)-2-(N-propylamino)-5-methoxytetraline, S-(II), obtained according to Example 1 were mixed with 13.8 g of K$_2$CO$_3$ (2.2 equivalents) and 15 g of 2-(2-thienyl)ethanol 2-nitrobenzenesulfonate (1.05 equivalents) in 60 mL of acetonitrile. The mixture was refluxed for 9 hours, and then cooled to room temperature. 80 mL of water were added and concentrated by distillation from acetonitrile. 40 mL of toluene were added and the layers were separated. The organic layer was twice washed with 40 mL of 5% NaHCO$_3$ by heating the biphasic mixture at 60° C. and finally washing with water Then, to the organic layer 40 mL of water and H$_3$PO$_4$ to pH=1-2) were added. After layer separation, the aqueous acid layer was basified with NaOH 10M to pH=11 and extracted with 30 mL of toluene. The organic layer was washed with 20 mL of water, concentrated by distillation until an oily product was obtained. The product was converted into its bromohydrate by redissolution in ethyl acetate and addition of HBr/AcOH. The solid formed was recovered by filtration and dried. 15.3 g of (S)-2-(N-n-propyl-N-2-thienylethylamino)-5-methoxitetraline bromohydrate, S-(IV).HBr, were obtained as a white solid (82% yield).

Melting point (DSC peak): 142.59° C.

IR (cm$^{-1}$, KBr): 2933, 2623, 2546, 1587, 1469, 1438, 1258, 1093, 772

$^1$H NMR (CDCl$_3$) δ: 1.01 (t, 3H), 1.90 (m, 1H), 2.08 (m, 1H), 2.59 (m, 2H), 3.00-3.70 (m, 11H), 3.78 (s, 1H, OCH3), 6.67 (d, 1H, Ar—H), 6.70 (d, 1H, Ar—H), 6.92 (m, 2H, Ar—H), 7.11 (t, 1H, Ar—H), 7.17 (d, 1H, Ar—H), 11.43 (s, 1H, NH)

EXAMPLE 6

Preparation of (6S)-(−)-5,6,7,8-tetrahydro-6-[propyl-(2-thienyl)ethyl]amino-1-naphthol, S-(I), from (S)-2-(N-n-propyl-N-2-thienylethylamino)-5-methoxytetraline bromohydrate, S-(IV).HBr 10 g of (S)-2-(N-n-propyl-N-2-thienylethylamino)-5-methoxytetraline bromohydrate, S-(IV).HBr, were dissolved in 50 mL of dichloromethane at room temperature. The mixture was cooled at a lower temperature than 0-5° C. 55 mL of a BBr$_3$ solution in dichloromethane (5 equivalents) were dropwise added, and the mixture was kept at 0-5° C. under stirring for 6 hours. 60 mL of water were added to the reaction mixture. A white solid precipitated which was recovered by filtration. The moist solid was suspended in 20 mL of water and 40 mL of ethyl acetate at room temperature. The mixture was basified to pH=7-7.5 with 30% K$_2$CO$_3$. The layers were separated and the aqueous layer was extracted with 20 mL of ethyl acetate which was combined with previous organic layer. The organic layer was washed with 10 mL of water and concentrated by distillation. 6.9 g of (6S)-(−)-5,6,7,8-tetrahydro-6-[propyl-(2-thienyl)ethyl]amino-1-naphthol, S-(I), were obtained as a white solid (90% yield).

Melting point (DSC peak): 78.37° C.

The invention claimed is:

1. A process for the preparation of optically active (S)-(−)-2-(N-propylamino)-5-methoxytetraline and (S)-(−)-2-(N-propylamino)-5-hydroxytetraline compounds having the formulas S-(II) and S-(III), respectively:

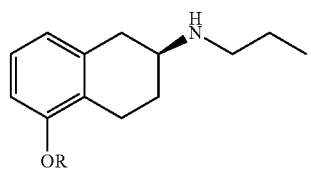

R = CH$_3$, S-(II)
R = H, S-(II)

which comprises the optical resolution of the corresponding compounds (II) and (III):

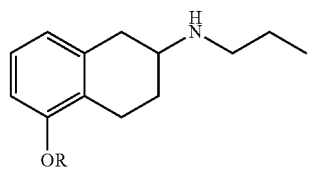

R = CH$_3$, (II)
R = H, (III)

with an optically active form of N-(3,5-dinitrobenzoyl)-α-phenylglycine, and which further comprises recrystallization in a solution of acetonitrile and water.

2. A process according to claim 1, wherein the preparation of the optically active S-(II) compound comprises the optical resolution of the corresponding compound (II) with (+)-N-(3,5-dinitrobenzoyl)-α-phenylglycine.

3. A process according to claim 1, wherein the preparation of the optically active S-(III) compound comprises the optical resolution of the corresponding compound (III) with (−)-N-(3,5-dinitrobenzoyl)-α-phenylglycine.

4. The process according to claim 2, wherein the optically active compound S-(II) is obtained at 99% purity or greater.

5. The process according to claim 3, wherein the optically active compound S-(III) is obtained at 99% purity or greater.

6. The process according to claim 2, wherein the optically active compound S-(II) is a salt, and wherein the salt is a salt of formula (V):

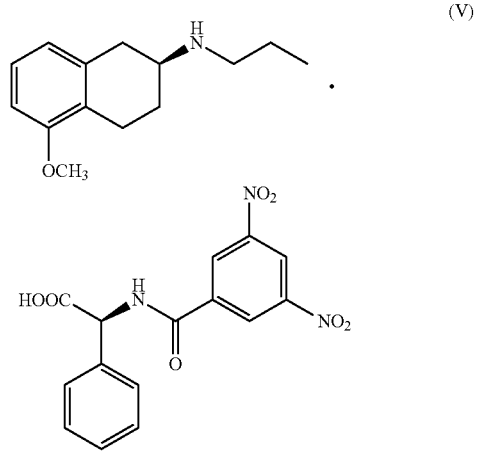

7. The process according to claim 3, wherein the optically active compound S-(III) is a salt, and wherein the salt is a salt of formula (VI):

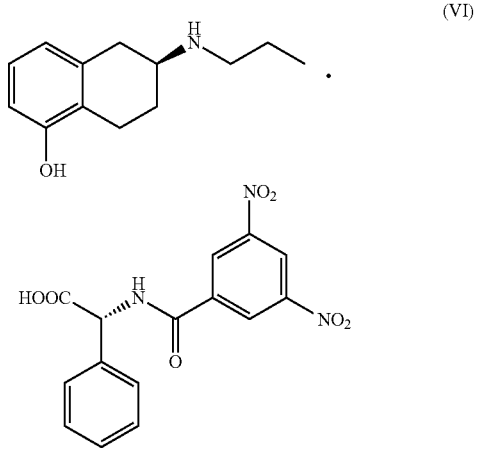

8. A process for the preparation of optically active (S)-(−)-2-(N-propylamino)-5-hydroxytetraline S-(III):

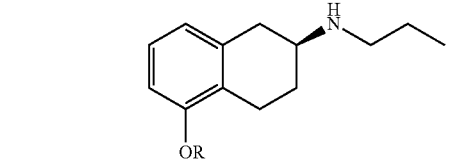

R = H, S-(III)

which comprises optical resolution of a corresponding compound (III):

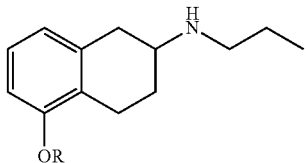

R = H, (III)

with an optically active form of N-(3,5-dinitrobenzoyl)-α-phenylglycine, and which further comprises recrystallization in a solution of acetonitrile and water.

9. The process according to claim 1, further comprising:
preparing (6S)-(−)-5,6,7,8-tetrahydro-6-[propyl-(2-thienyl)ethyl]amino-1-naphthol (Rotigotine) from optically active S-(II).

10. The process according to claim 1, further comprising:
preparing (6S)-(−)-5,6,7,8-tetrahydro-6-[propyl-(2-thienyl)ethyl]amino-1-naphthol (Rotigotine) from optically active S-(III).

11. The salt formed between (S)-(−)-2-(N-propylamino)-5-methoxytetraline, S-(II), and (+)-N-(3,5-dinitrobenzoyl)-α-phenylglycine acid of formula (V):

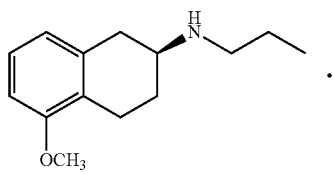

(V)

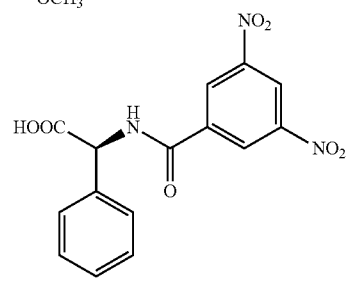

12. The salt formed between (S)-(−)-2-(N-propylamino)-5-hydroxytetraline, S-(III), and (−)-N-(3,5-dinitrobenzoyl)-α-phenylglycine acid of formula (VI):

(VI)

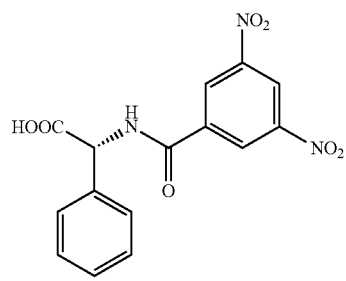

13. A process of preparing (6S)-(−)-5,6,7,8-tetrahydro-6-[propyl-(2-thienyl)ethyl]amino-1-naphthol (Rotigotine) which comprises:
preparing (6S)-(−)-5,6,7,8-tetrahydro-6-[propyl-(2-thienyl)ethyl]amino-1-naphthol (Rotigotine) from the salt of formula (V) of claim 11.

14. A process of preparing (6S)-(−)-5,6,7,8-tetrahydro-6-[propyl-(2-thienyl)ethyl]amino-1-naphthol (Rotigotine) which comprises:
preparing (6S)-(−)-5,6,7,8-tetrahydro-6-[propyl-(2-thienyl)ethyl]amino-1-naphthol (Rotigotine) from the salt of formula (VI) of claim 12.

* * * * *